US012097010B2

(12) United States Patent
Jin et al.

(10) Patent No.: US 12,097,010 B2
(45) Date of Patent: Sep. 24, 2024

(54) MAINTAINING CONSISTENT PHOTODETECTOR SENSITIVITY IN AN OPTICAL MEASUREMENT SYSTEM

(71) Applicant: HI LLC, Los Angeles, CA (US)

(72) Inventors: Rong Jin, Acton, MA (US); Sebastian Sorgenfrei, Playa Vista, CA (US); Ryan Field, Culver City, CA (US); Bruno Do Valle, Brighton, MA (US); Jacob Dahle, Arlington, MA (US)

(73) Assignee: HI LLC, Culver City, CA (US)

( * ) Notice: Subject to any disclaimer, the term of this patent is extended or adjusted under 35 U.S.C. 154(b) by 0 days.

(21) Appl. No.: 18/379,516

(22) Filed: Oct. 12, 2023

(65) Prior Publication Data

US 2024/0032798 A1 Feb. 1, 2024

Related U.S. Application Data

(62) Division of application No. 17/202,563, filed on Mar. 16, 2021, now Pat. No. 11,819,311.

(Continued)

(51) Int. Cl.
*A61B 5/00* (2006.01)

(52) U.S. Cl.
CPC .......... *A61B 5/0082* (2013.01); *A61B 5/0073* (2013.01); *A61B 5/0075* (2013.01);
(Continued)

(58) Field of Classification Search
CPC ... A61B 5/0082; A61B 5/0073; A61B 5/0075; A61B 5/4064; A61B 5/6803;
(Continued)

(56) References Cited

U.S. PATENT DOCUMENTS 5,218,962 A 6/1993 Mannheimer et al.
5,853,370 A 12/1998 Chance et al.
(Continued)

FOREIGN PATENT DOCUMENTS

FR 3011932 A1 4/2015
JP 2012125370 A 1/2015

OTHER PUBLICATIONS

Alayed, et al., Characterization of a Time-Resolved Diffuse Optical Spectroscopy Prototype Using Low-Cost, Compact Single Photon Avalanche Detectors for Tissue Optics Applications, Sensors 2018, 18, 3680; doi:10.3390/s18113680, Oct. 29, 2018.
(Continued)

*Primary Examiner* — Seung C Sohn
(74) *Attorney, Agent, or Firm* — ALG Intellectual Property, LLC

(57) ABSTRACT

An illustrative optical measurement system includes a light source configured to emit light directed at a target. The optical measurement system further includes a photodetector configured to detect a photon of the light after the light is scattered by the target. The optical measurement system further includes a control circuit configured to receive a first input voltage that is a temperature-dependent voltage. The control circuit is further configured to receive a second input voltage that is a temperature-invariant voltage. The control circuit is further configured to output, based on a combination of the first input voltage and the second input voltage, a bias voltage for the photodetector, wherein the combination of the first and second input voltages is configured to cause the bias voltage to vary based on temperature.

15 Claims, 18 Drawing Sheets

Related U.S. Application Data

(60) Provisional application No. 63/064,249, filed on Aug. 11, 2020, provisional application No. 62/992,493, filed on Mar. 20, 2020.

(52) U.S. Cl.
CPC .......... *A61B 5/4064* (2013.01); *A61B 5/6803* (2013.01); *A61B 2560/0214* (2013.01)

(58) Field of Classification Search
CPC .... A61B 2560/0214; A61B 2562/0238; A61B 2576/026; A61B 5/0059; G01J 2001/442; G01J 1/0252; G01J 1/44; G01S 7/4863; G01S 17/18
See application file for complete search history.

(56) References Cited

U.S. PATENT DOCUMENTS

| | | | |
|---|---|---|---|
| 5,924,982 | A | 7/1999 | Chin |
| 6,195,580 | B1 | 2/2001 | Grable |
| 6,240,309 | B1 | 5/2001 | Yamashita et al. |
| 6,291,842 | B1 | 9/2001 | Nakayama |
| 6,384,663 | B2 | 5/2002 | Cova et al. |
| 6,542,763 | B1 | 4/2003 | Yamashita et al. |
| 6,640,133 | B2 | 10/2003 | Yamashita et al. |
| 6,683,294 | B1 | 1/2004 | Herbert et al. |
| 7,356,365 | B2 | 4/2008 | Schurman |
| 7,547,872 | B2 | 6/2009 | Niclass et al. |
| 7,774,047 | B2 | 8/2010 | Yamashita et al. |
| 7,888,973 | B1 | 2/2011 | Rezzi et al. |
| 8,026,471 | B2 | 9/2011 | Itzler |
| 8,078,250 | B2 | 12/2011 | Chen et al. |
| 8,082,015 | B2 | 12/2011 | Yodh et al. |
| 8,269,563 | B2 | 9/2012 | Ballantyne |
| 8,633,431 | B2 | 1/2014 | Kim |
| 8,817,257 | B2 | 8/2014 | Herve |
| 9,058,081 | B2 | 6/2015 | Baxter |
| 9,076,707 | B2 | 7/2015 | Harmon |
| 9,131,861 | B2 | 9/2015 | Ince et al. |
| 9,316,735 | B2 | 4/2016 | Baxter |
| 9,401,448 | B2 | 7/2016 | Bienfang et al. |
| 9,419,635 | B2 | 8/2016 | Kumar et al. |
| 9,442,201 | B2 | 9/2016 | Schmand et al. |
| 9,529,079 | B1 | 12/2016 | Droz et al. |
| 9,554,738 | B1 | 1/2017 | Gulati et al. |
| 9,574,936 | B2 | 2/2017 | Heinonen |
| 9,946,344 | B2 | 4/2018 | Ayaz et al. |
| D817,553 | S | 5/2018 | Aaskov et al. |
| 9,983,670 | B2 | 5/2018 | Coleman et al. |
| D825,112 | S | 8/2018 | Saez |
| 10,154,815 | B2 | 12/2018 | Al-Ali et al. |
| 10,158,038 | B1 | 12/2018 | Do et al. |
| 10,340,408 | B1 | 7/2019 | Katnani et al. |
| 10,424,683 | B1 | 9/2019 | Valle et al. |
| 10,515,993 | B2 | 12/2019 | Field et al. |
| 10,697,829 | B2 | 6/2020 | Delic |
| 10,772,561 | B2 | 9/2020 | Donaldson |
| 10,809,796 | B2 | 10/2020 | Armstrong-Muntner et al. |
| 10,912,504 | B2 | 2/2021 | Nakaji et al. |
| 11,006,876 | B2 | 5/2021 | Johnson et al. |
| 11,006,878 | B2 | 5/2021 | Johnson et al. |
| 11,213,245 | B2 | 1/2022 | Horstmeyer et al. |
| 2002/0033454 | A1 | 3/2002 | Cheng et al. |
| 2004/0064052 | A1 | 4/2004 | Chance et al. |
| 2005/0059869 | A1 | 3/2005 | Scharf et al. |
| 2007/0083097 | A1 | 4/2007 | Fujiwara et al. |
| 2009/0012402 | A1 | 1/2009 | Mintz et al. |
| 2010/0007413 | A1 | 1/2010 | Herleikson et al. |
| 2011/0208675 | A1 | 8/2011 | Shoureshi et al. |
| 2013/0153754 | A1 | 6/2013 | Drader et al. |
| 2013/0300838 | A1 | 11/2013 | Borowski et al. |
| 2013/0342835 | A1 | 12/2013 | Blacksberg |
| 2014/0191115 | A1 | 7/2014 | Webster et al. |
| 2014/0217264 | A1 | 8/2014 | Shepard et al. |
| 2014/0275891 | A1 | 9/2014 | Muehlemann et al. |
| 2015/0011848 | A1 | 1/2015 | Ruchti et al. |
| 2015/0038811 | A1 | 2/2015 | Asaka et al. |
| 2015/0041625 | A1 | 2/2015 | Dutton et al. |
| 2015/0054111 | A1 | 2/2015 | Niclass et al. |
| 2015/0077279 | A1 | 3/2015 | Song et al. |
| 2015/0150505 | A1 | 6/2015 | Kaskoun et al. |
| 2015/0327777 | A1 | 11/2015 | Kostic et al. |
| 2015/0355019 | A1 | 12/2015 | Nouri et al. |
| 2015/0364635 | A1 | 12/2015 | Bodlovic et al. |
| 2016/0349368 | A1 | 12/2016 | Stutz et al. |
| 2017/0030769 | A1 | 2/2017 | Clemens et al. |
| 2017/0052065 | A1 | 2/2017 | Sharma et al. |
| 2017/0172447 | A1 | 6/2017 | Mitra et al. |
| 2017/0176596 | A1 | 6/2017 | Shpunt et al. |
| 2017/0179173 | A1 | 6/2017 | Mandai et al. |
| 2017/0202518 | A1 | 7/2017 | Furman et al. |
| 2017/0281086 | A1 | 10/2017 | Donaldson |
| 2017/0338969 | A1 | 11/2017 | Paul et al. |
| 2017/0363467 | A1 | 12/2017 | Clemens et al. |
| 2017/0367650 | A1 | 12/2017 | Wallois et al. |
| 2018/0014741 | A1 | 1/2018 | Chou |
| 2018/0027196 | A1 | 1/2018 | Yang et al. |
| 2018/0033751 | A1 | 2/2018 | Ban et al. |
| 2018/0039053 | A1 | 2/2018 | Kremer et al. |
| 2018/0070830 | A1 | 3/2018 | Sutin et al. |
| 2018/0070831 | A1 | 3/2018 | Sutin et al. |
| 2018/0089848 | A1 | 3/2018 | Yang et al. |
| 2018/0090536 | A1 | 3/2018 | Mandai et al. |
| 2018/0180473 | A1 | 6/2018 | Clemens et al. |
| 2018/0192931 | A1 | 7/2018 | Linden et al. |
| 2019/0113385 | A1 | 4/2019 | Fukuchi |
| 2019/0175068 | A1 | 6/2019 | Everdell |
| 2019/0239753 | A1 | 8/2019 | Wentz |
| 2019/0355861 | A1 | 11/2019 | Katnani et al. |
| 2019/0363210 | A1 | 11/2019 | Valle et al. |
| 2019/0388018 | A1 | 12/2019 | Horstmeyer et al. |
| 2020/0057146 | A1 | 2/2020 | Steinkogler et al. |
| 2020/0060542 | A1 | 2/2020 | Alford et al. |
| 2020/0116838 | A1 | 4/2020 | Erdogan et al. |
| 2020/0196932 | A1 | 6/2020 | Johnson et al. |
| 2020/0253479 | A1 | 8/2020 | Nurmikko |
| 2020/0315510 | A1 | 10/2020 | Johnson et al. |
| 2020/0337624 | A1 | 10/2020 | Johnson et al. |
| 2020/0379095 | A1 | 12/2020 | Kappel et al. |
| 2020/0390358 | A1 | 12/2020 | Johnson et al. |
| 2021/0186138 | A1 | 6/2021 | Bartels et al. |
| 2021/0223098 | A1 | 7/2021 | Ledvina et al. |

OTHER PUBLICATIONS

Ban, et al., Kernel Flow: a high channel count scalable TD-fNIRS system, https://www.spiedigitallibrary.org/conference-proceedings-of-spie Proc. of SPIE vol. 11663, 116630B doi: 10.1117/12.2582888, Mar. 5, 2021.

Ban, et al., Kernel Flow: a high channel count scalable time-domain functional near-infrared spectroscopy system, https://www.spiedigitallibrary.org/journals/Journal-of-Biomedical-Optics on Jan. 18, 2022.

Contini, et al., Photon migration through a turbid slab described by a model based on diffusion approximation. I. Theory, Appl. Opt. 36(19), 4587 (1997).

Di Sieno, et al., Probe-hosted large area silicon photomultiplier and high-throughput timing electronics for enhanced performance time-domain functional near-infrared spectroscopy, Biomed. Opt. Express 11(11), 6389 (2020).

Fishburn, et al., Temporal Derivative Distribution Repair (TDDR): A motion correction method for fNIRS, Neuroimage. Jan. 1, 2019; 184: 171-179. doi:10.1016/j.neuroimage.2018.09.025.

Huppert, et al., HomER: a review of time-series analysis methods for near-infrared spectroscopy of the brain, Appl. Opt. 48(10), D280 (2009).

Kienle, et al., Improved solutions of the steady-state and the time-resolved diffusion equations for reflectance from a semi-infinite turbid medium, J. Opt. Soc. Am. A 14(1), 246 (1997).

(56) References Cited

OTHER PUBLICATIONS

Konugolu, et al., Broadband (600-1350 nm) Time-Resolved Diffuse Optical Spectrometer for Clinical Use, IEEE Journal of Selected Topics in Quantum Electronics, vol. 22, No. 3, May/Jun. 2016.

Lacerenza, et al., Wearable and wireless time-domain near-infrared spectroscopy system for brain and muscle hemodynamic monitoring, Biomed. Opt. Express 11(10), 5934 (2020).

Lange, et al., Clinical Brain Monitoring with Time Domain NIRS: A Review and Future Perspectives, Applied Sciences 9(8), 1612 (2019).

Lange, et al., Maestros: A Multiwavelength Time-Domain NIRS System to Monitor Changes in Oxygenation and Oxidation State of Cytochrome-C-Oxidase, IEEE J. Select. Topics Quantum Electron. 25(1), 1-12 (2019).

Martelli, et al., Optimal estimation reconstruction of the optical properties of a two-layered tissue phantom from time-resolved single-distance measurements, Journal of Biomedical Optics 20(11), 115001 (Nov. 2015).

Mora, et al., Fast silicon photomultiplier improves signal harvesting and reduces complexity in time-domain diffuse optics, Opt. Express 23(11), 13937 (2015).

Pifferi, et al., Performance assessment of photon migration instruments: the MEDPHOT protocol, Applied Optics, 44 (11), 2104-2114, 2005.

Prahl, Optical Absorption of Hemoglobin, http://omlc.ogi.edu/spectra/hemoglobin/index.html, 1999.

Re, et al., Multi-channel medical device for time domain functional near infrared spectroscopy based on wavelength space multiplexing, Biomed. Opt. Express 4(10), 2231 (2013).

Renna, et al., Eight-Wavelength, Dual Detection Channel Instrument for Near-Infrared Time-Resolved Diffuse Optical Spectroscopy, IEEE J. Select. Topics Quantum Electron. 25(1), 1-11 (2019).

Torricelli, et al., Time domain functional NIRS imaging for human brain mapping, NeuroImage 85, 28-50 (2014).

Wabnitz, et al., Depth-selective data analysis for time-domain fNIRS: moments vs. time windows, Biomed. Opt. Express 11(8), 4224 (2020).

Wabnitz, et al., Performance assessment of time-domain optical brain imagers, part 1: basic instrumental performance protocol, Journal of Biomedical Optics 19(8), 086010 (Aug. 2014).

Wabnitz, et al., Performance assessment of time-domain optical brain imagers, part 2: nEUROPt protocol, Journal of Biomedical Optics 19(8), 086012 (Aug. 2014).

Wojtkiewicz, et al., Self-calibrating time-resolved near infrared spectroscopy, Biomed. Opt. Express 10(5), 2657 (2019).

Zucchelli, et al., Method for the discrimination of superficial and deep absorption variations by time domain fNIRS, 2013 OSA Dec. 1, 2013 | vol. 4, No. 12 | DOI:10.1364/BOE.4.002893 | Biomedical Optics Express 2893, 2013.

MAINTAINING CONSISTENT PHOTODETECTOR SENSITIVITY IN AN OPTICAL MEASUREMENT SYSTEM

RELATED APPLICATIONS

The present application is a divisional of U.S. patent application Ser. No. 17/202,563, filed Mar. 16, 2021, which claims priority under 35 U.S.C. § 119(e) to U.S. Provisional Patent Application No. 62/992,493, filed Mar. 20, 2020, and to U.S. Provisional Patent Application No. 63/064,249, filed Aug. 11, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

An optical measurement system as described herein may include a plurality of photodetectors each configured to detect photons of light after the light is scattered by a target (e.g., a brain of a user). Unfortunately, the sensitivity of photodetectors may vary based on temperature. This is because sensitivity of a photodetector is at least in part dependent on an overvoltage for the photodetector, where the overvoltage refers to a difference between a bias voltage used to arm the photodetector and a breakdown voltage of the photodetector. As described herein, the breakdown voltage of a photodetector varies with temperature, which in turn can cause the overvoltage (and hence, the sensitivity) of the photodetector to also vary. This photodetector sensitivity variation may skew or otherwise negatively affect measurements performed by the optical measurement system.

The systems, circuits, and methods described herein may be configured to compensate for such photodetector sensitivity variation by outputting a bias voltage for one or more photodetectors that is also configured to vary based on the temperature, but in a controlled manner. For example, a control circuit may be configured to receive a first input voltage that is a temperature-dependent voltage and a second input voltage that is a temperature-invariant voltage. Based on the combination of the first input voltage and the second input voltage, the control circuit may output a bias voltage for a photodetector. As described herein, the combination of the first and second input voltages is configured to cause the bias voltage to vary in a controlled manner based on temperature. This may allow for a voltage difference between the bias voltage and a breakdown voltage of the photodetector to remain at least a predetermined voltage amount. The maintained voltage difference may allow the photodetector to maintain a substantially consistent sensitivity, even as temperature varies.

As described herein, the systems, circuits, and methods may conserve power and reduce complexity compared to conventional approaches used to attempt to maintain consistent photodetector sensitivity. These and other advantages and benefits of the present systems, circuits, and methods are described more fully herein.

Figure 1:
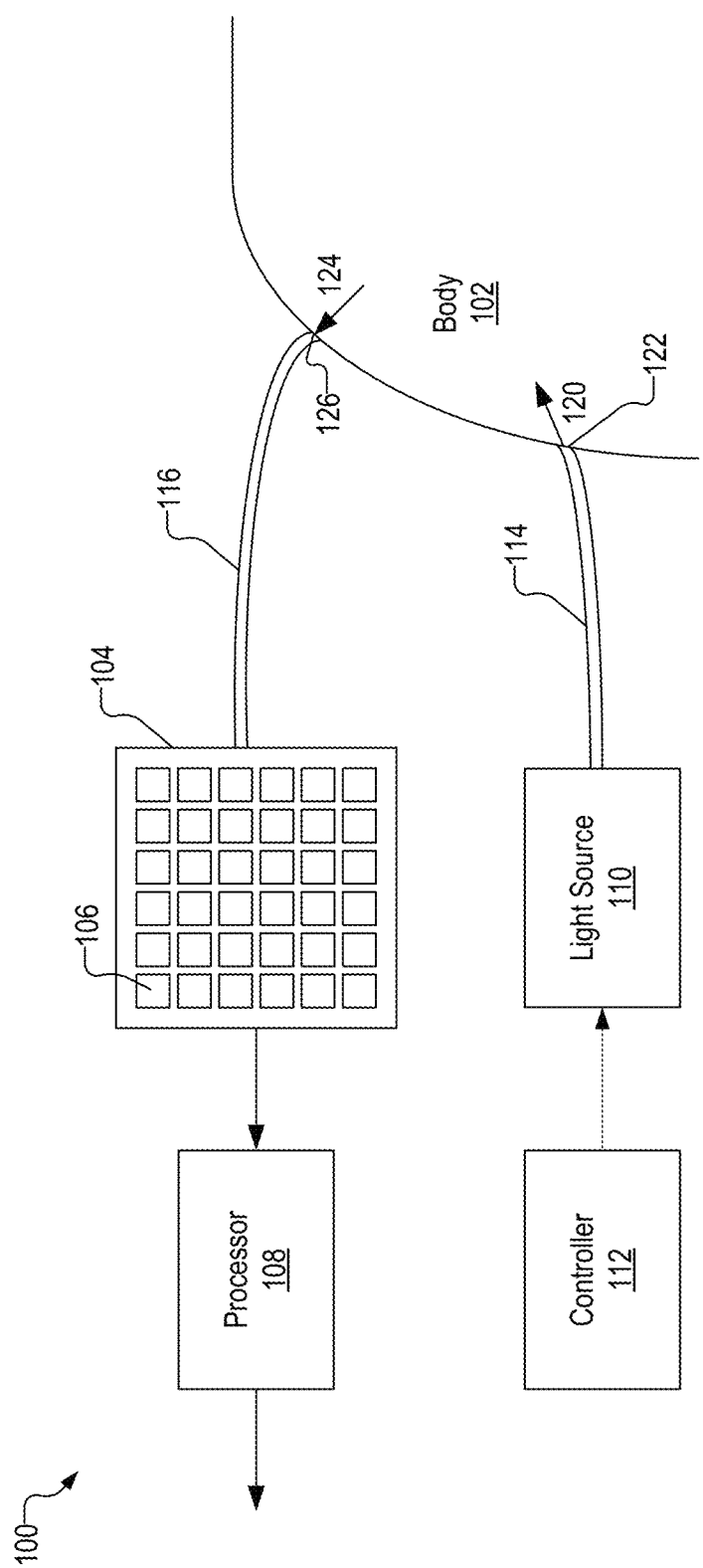
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain Digital Optical Tomography (TD-DOT). For example, TCSPC detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, ..., 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diode (mLEDs), and/or any other suitable laser or light source. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. Accordingly, a distal end of optical conduit 114 may be positioned at (e.g., right above or physically attached to) first location 122 (e.g., to a scalp of the subject). In some examples, the light may emerge from optical conduit 114 and spread out to a certain spot size on body 102 to fall under a predetermined safety limit.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a single-mode optical fiber, and/or or a multi-mode optical fiber) is positioned at (e.g., right above or physically attached to) output location 126 on body 102. In this manner, optical conduit 116 may collect light 124 as it exits body 102 at location 126 and carry the light to detector 104. The light may pass through one or more lenses and/or other optical elements (not shown) that direct the light onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
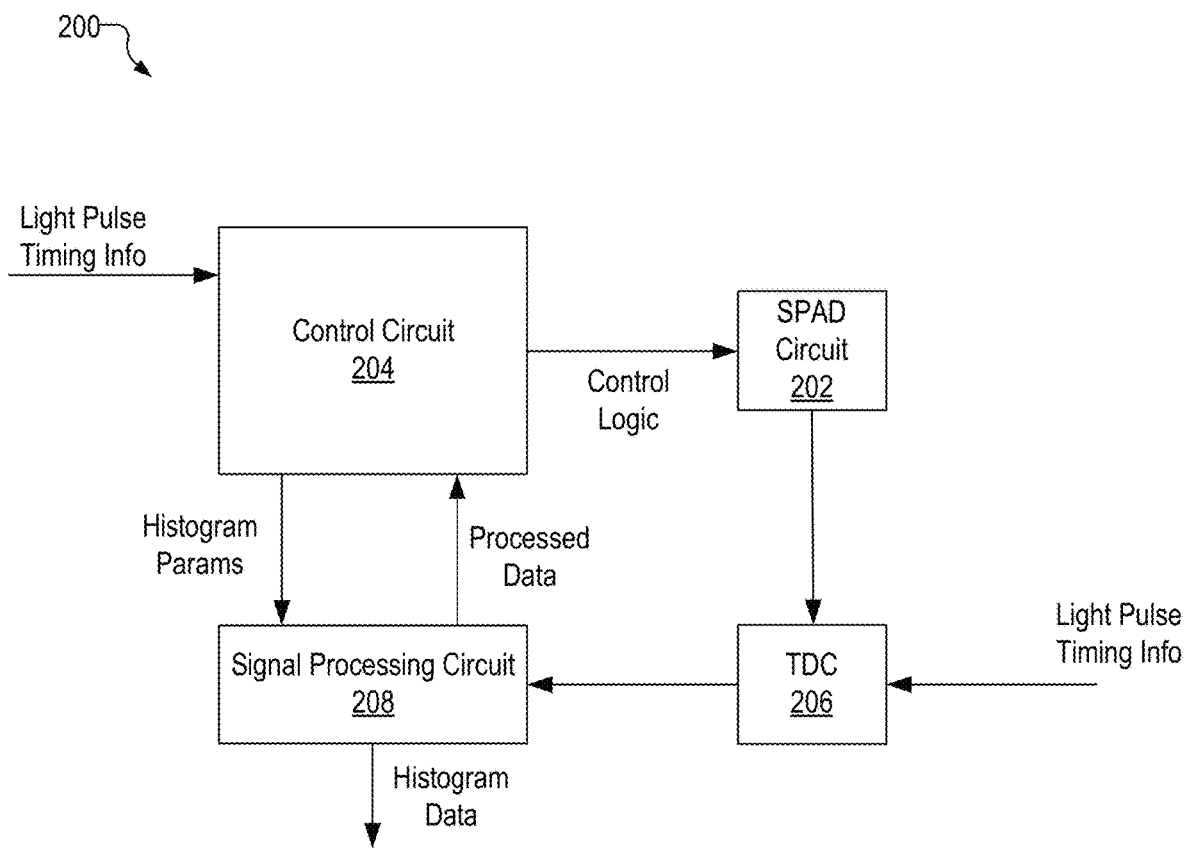
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
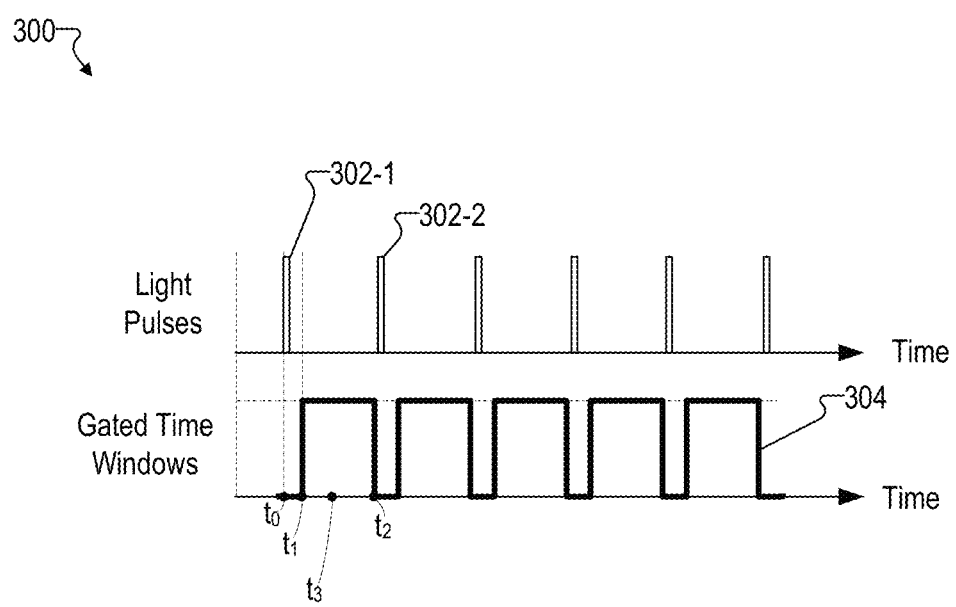
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. Referring to light pulse 302-1, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
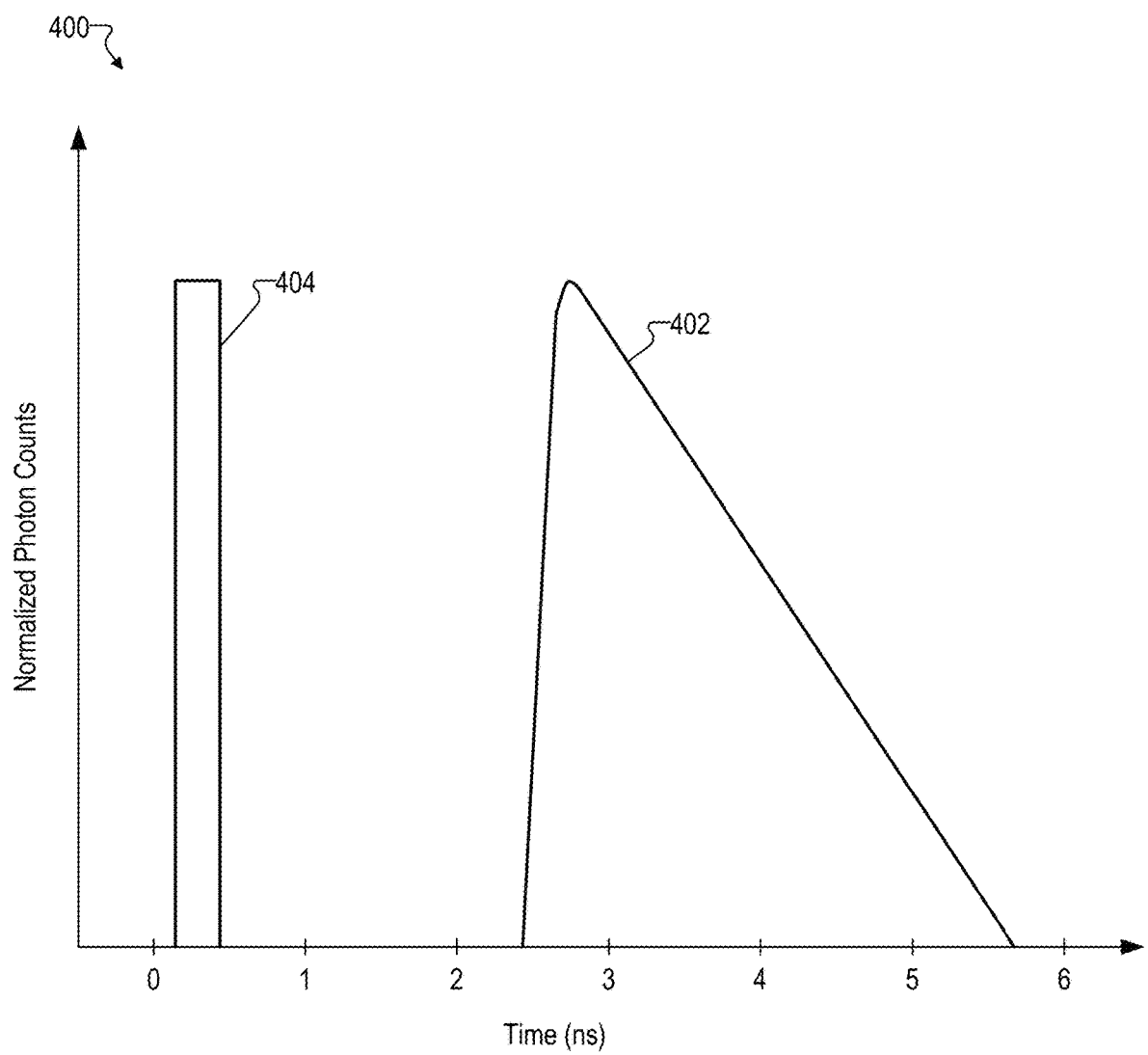
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
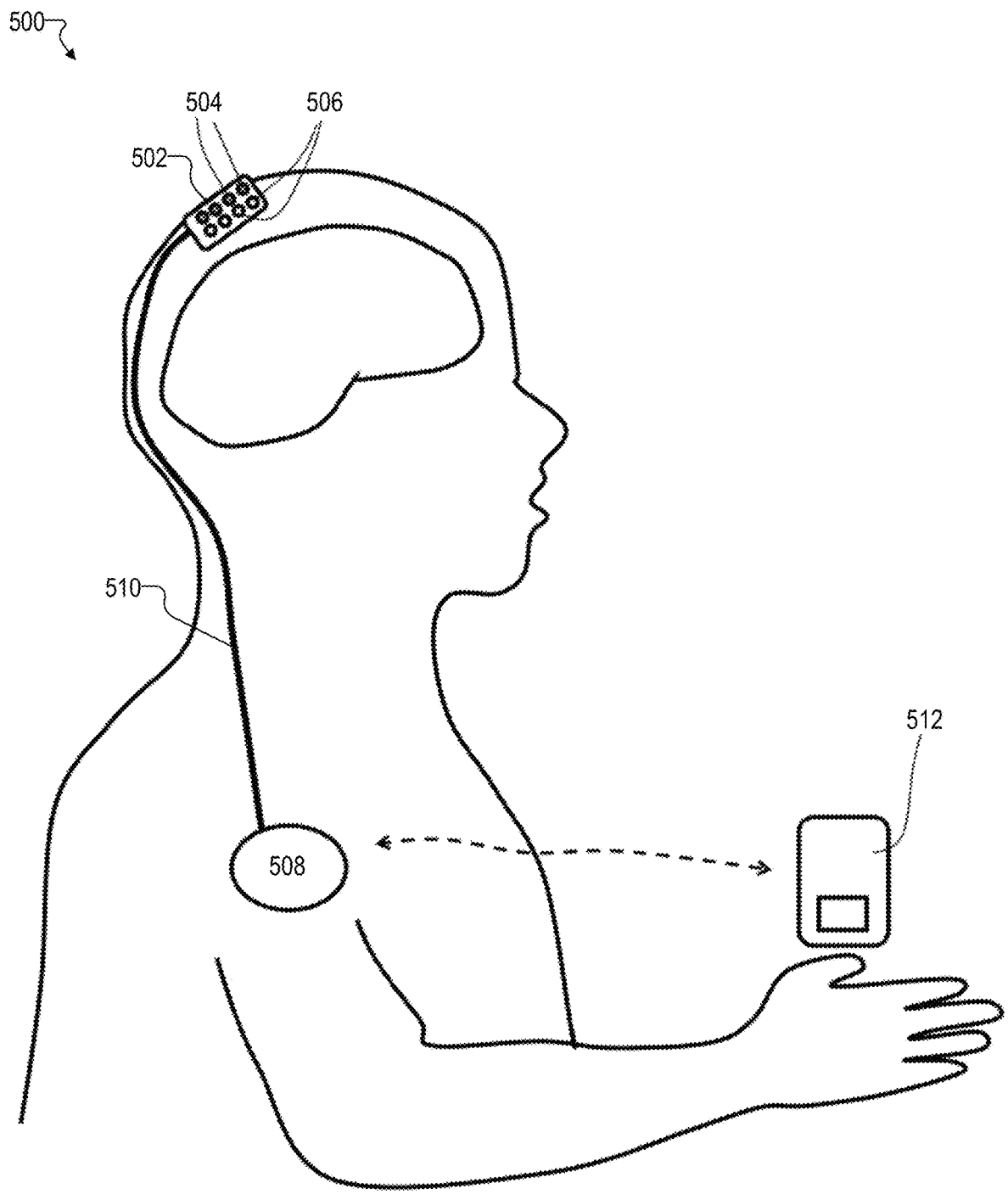
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

Figure 6:
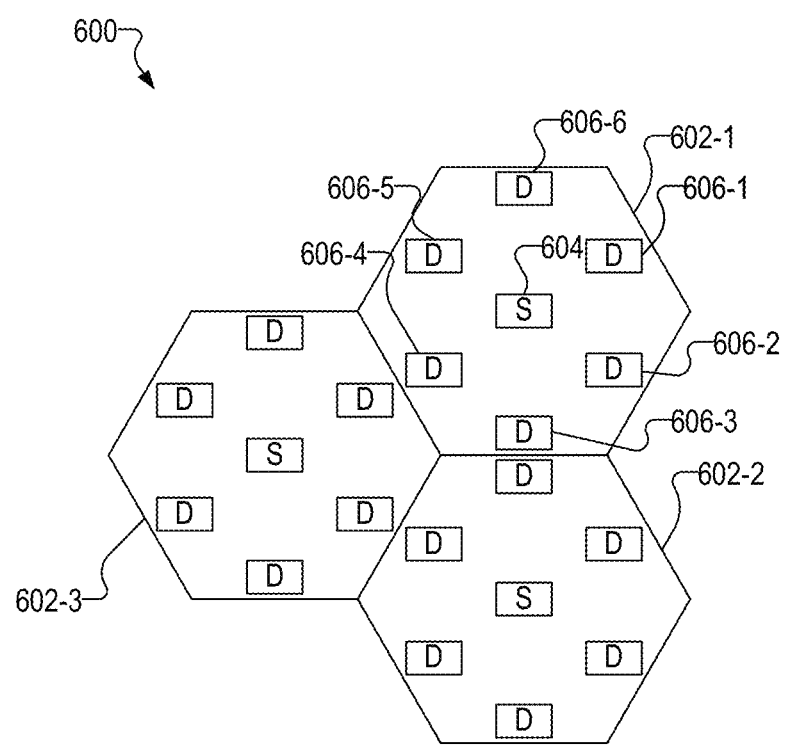
FIG. 6 shows an exemplary wearable module assembly.

To illustrate, FIG. 6 shows an exemplary wearable module assembly 600 ("assembly 600") that implements one or more of the optical measurement features described herein. Assembly 600 may be worn on the head or any other suitable body part of the user. As shown, assembly 600 may include a plurality of modules 602 (e.g., modules 602-1 through 602-3). While three modules 602 are shown to be included in assembly 600 in FIG. 6, in alternative configurations, any number of modules 602 (e.g., a single module up to sixteen or more modules) may be included in assembly 600. Moreover, while modules 602 are shown to be adjacent to and touching one another, modules 602 may alternatively be spaced apart from one another (e.g., in implementations where modules 602 are configured to be inserted into individual slots or cutouts of the headgear). Moreover, while modules 602 are shown to have a hexagonal shape, modules 602 may alternatively have any other suitable geometry (e.g., in the shape of a pentagon, octagon, square, rectangular, circular, triangular, free-form, etc.). Assembly 600 may conform to three-dimensional surface geometries, such as a user's head. Exemplary wearable module assemblies comprising a plurality of wearable modules are described in more detail in U.S. Provisional Patent Application No. 62/992,550, filed Mar. 20, 2020, U.S. Provisional Patent Application No. 63/038,459, filed Jun. 12, 2020, and U.S. Provisional Patent Application No. 63/038,468, filed Jun. 12, 2020, which applications are incorporated herein by reference in their respective entireties.

Each module 602 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors (e.g., SPADs) as well as other circuitry (e.g., TDCs). As shown, detectors 606 are arranged around and substantially equidistant from source 604. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light emitter and the detector allows subsequent processing of the detected signals to infer spatial (e.g., depth localization, inverse modeling) information about the detected signals. Detectors 606 may be alternatively disposed as may serve a particular implementation.

Figure 7:
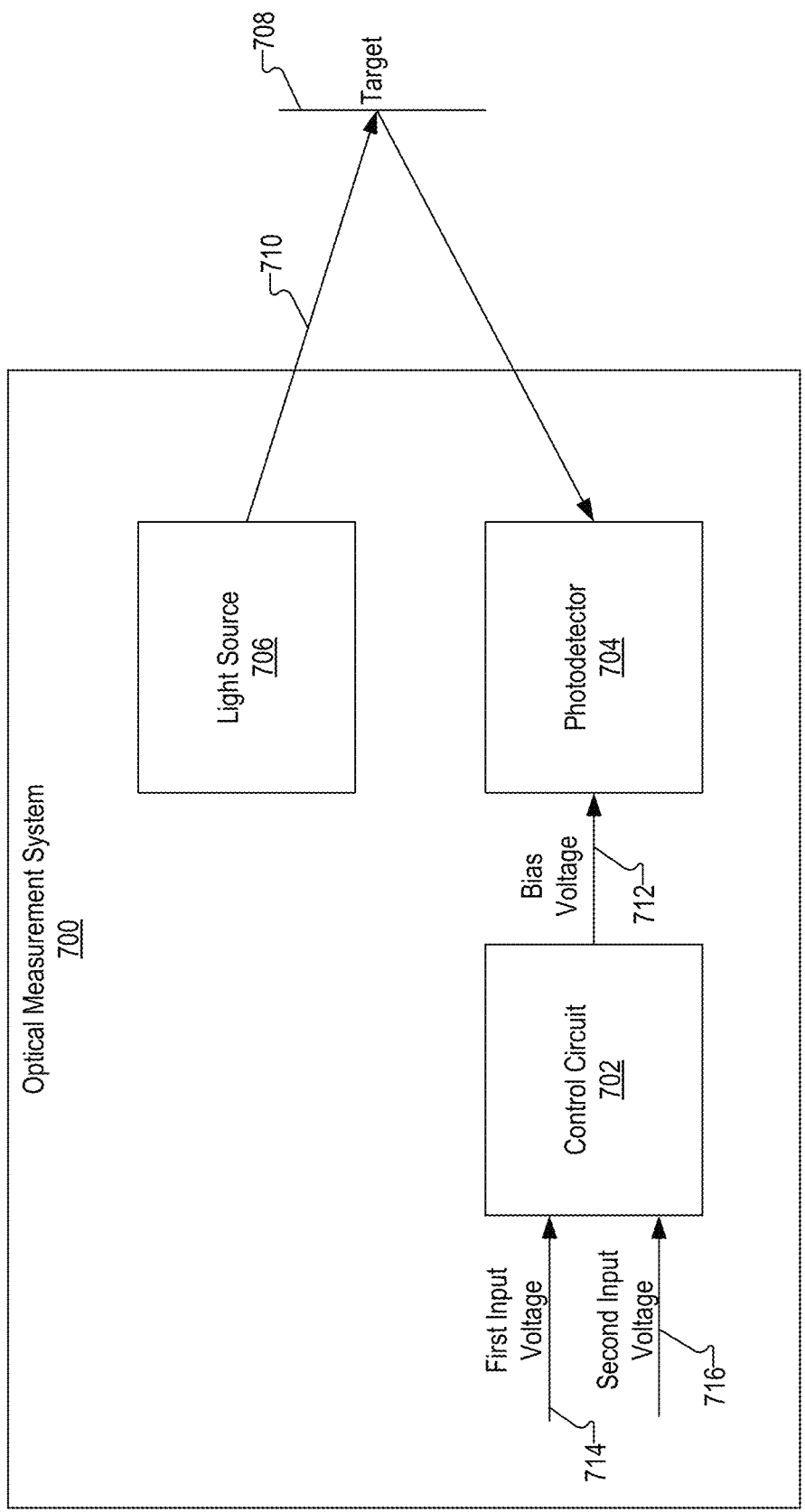
FIGS. 7-10 show exemplary configurations of an optical measurement system.

FIG. 7 shows an exemplary optical measurement system 700, which may be an implementation or a portion of optical measurement system 100. Optical measurement system 700 includes a control circuit 702 (e.g., an implementation or portion of control circuit 204 and/or processor 508), a photodetector 704 (e.g., an implementation of photodetector 106, SPAD circuit 202, etc.), and a light source 706 (e.g., an implementation of light source 110). Light source 706 may be configured to emit light directed toward a target 708 (e.g., a body of a user), as shown by an arrow 710. Photodetector 704 may be configured to detect one or more photons of the light after the light is scattered by target 708.

Control circuit 702 may be configured to output to photodetector 704 a bias voltage 712 that is used to arm photodetector 704 to detect photons. Bias voltage 712 may be configured to have a voltage level that is a predetermined voltage level greater than a breakdown voltage of photodetector 704.

The voltage level difference between bias voltage 712 and the breakdown voltage may define an overvoltage for photodetector 704, which may affect a sensitivity of photodetector 704. For example, the breakdown voltage may be temperature dependent such that an increase in temperature may result in an increase in the breakdown voltage. If the voltage level of bias voltage 712 remains constant while the breakdown voltage increases, the overvoltage may decrease, which may result in a decreased sensitivity of photodetector 704.

Control circuit 702 may be configured to output bias voltage 712 so that bias voltage 712 varies based on the temperature. For example, control circuit 702 may configure the voltage level of bias voltage 712 to vary based on temperature at a same rate as the breakdown voltage varies based on temperature. In this manner, control circuit 702 may configure bias voltage 712 to remain a predetermined voltage level above the breakdown voltage even as the breakdown voltage varies with changes in temperature. As a result, the overvoltage for photodetector 704 and the sensitivity of photodetector 704 may be kept substantially constant.

Control circuit 702 may be configured to vary bias voltage 712 based on temperature by basing bias voltage 712 on a first input voltage 714 that is temperature dependent and a second input voltage 716 that is temperature invariant. For instance, control circuit 702 may receive a proportional-toabsolute temperature (PTAT) voltage or any other suitable temperature-dependent voltage as first input voltage 714. Control circuit 702 may receive a bandgap voltage or any other suitable temperature-invariant voltage as second input voltage 716. Control circuit 702 may base bias voltage 712 on first input voltage 714 and second input voltage 716 by outputting a combination (e.g., a linear combination) of first input voltage 714 and second input voltage 716 that causes bias voltage 712 to vary with temperature at a same rate as the breakdown voltage. The rate of change of the breakdown voltage to temperature may be determined in any suitable manner (e.g., based on measurements performed during a testing period, such as during manufacturing, calibration, and/or any other quality control testing periods, based on measurements performed during operation, etc.).

The combination of first input voltage 714 and second input voltage 716 may be configured to vary at the rate of change of the breakdown voltage in any suitable manner. For instance, control circuit 702 may include a charge pump that receives first input voltage 714 and second input voltage 716 and outputs a linear combination of first input voltage 714 and second input voltage 716 that corresponds to the rate of change of the breakdown voltage, as described herein.

Figure 8:
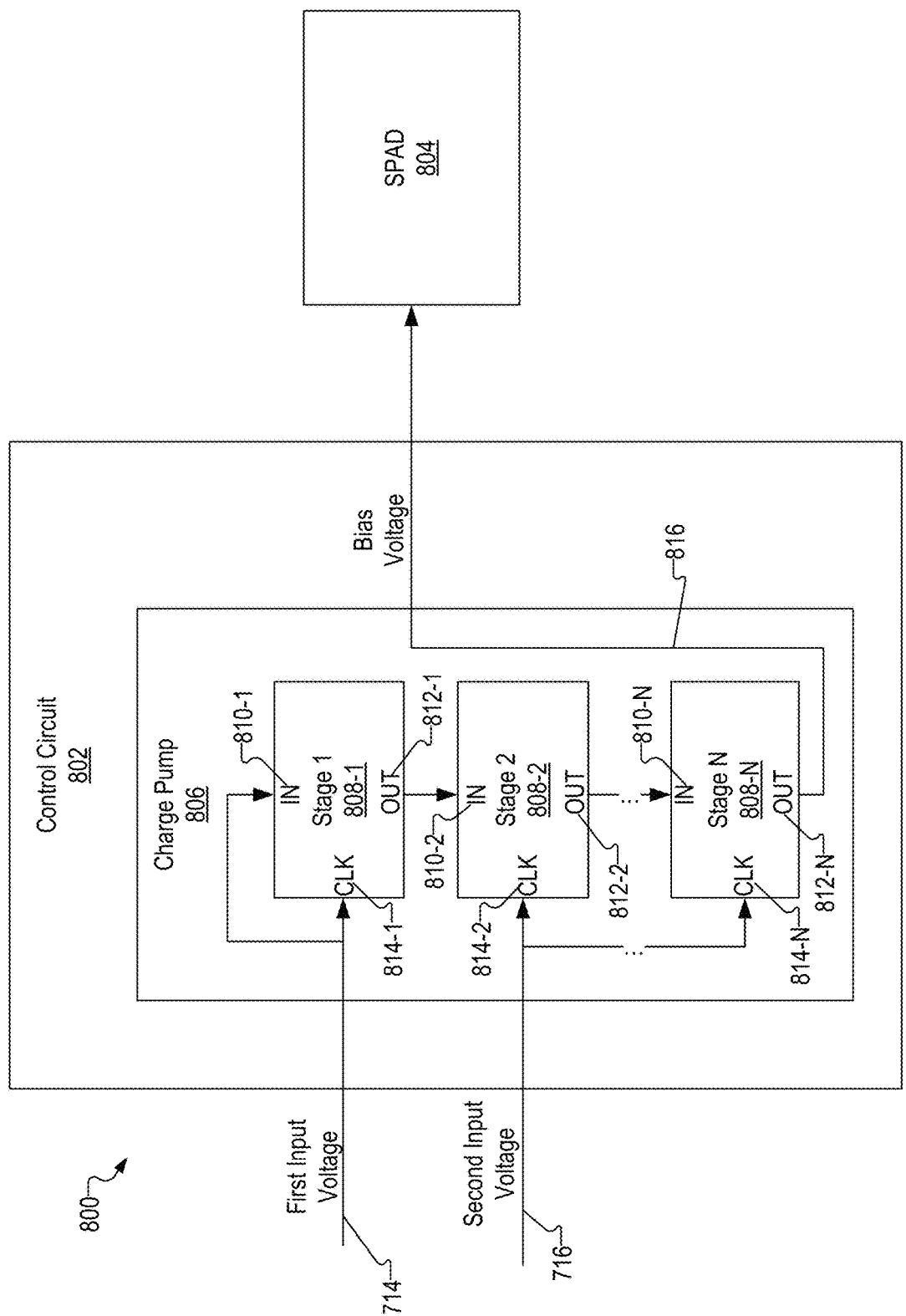

FIG. 8 shows an exemplary configuration 800 of components of an optical measurement system (e.g., optical measurement system 700). Configuration 800 includes a control circuit 802 (e.g., an implementation of control circuit 702) and a SPAD 804 (e.g., an implementation of photodetector 704).

Control circuit 802 includes a charge pump 806, which includes a plurality of charge pump stages 808 (e.g., charge pump stage 808-1 through charge pump stage 808-N). The total number of charge pump stages 808 included in control circuit 802 may be any suitable value. Each charge pump stage 808 includes an input 810 (e.g., input 810-1 through 810-N), an output 812 (e.g., output 812-1 through 812-N), and a clock input (e.g., clock input 814-1 through 814-N).

As shown, charge pump stages 808 are cascaded so that an output of each charge pump stage 808 is provided as an input to a next charge pump stage 808. For instance, charge pump 806 receives first input voltage 714, which charge pump stage 808-1 receives at input 810-1. Charge pump stage 808-1 may provide at output 812-1 an output voltage that is received by charge pump stage 808-2 at input 810-2. Charge pump stage 808-2 may provide at output 812-2 an output voltage that is received at a third input by a third charge pump stage (not shown), and so forth for all charge pump stages 808 up to charge pump stage 808-N. An output of charge pump stage 808-N may be provided as an output voltage 816 of charge pump 806.

Further, each charge pump stage 808 may be configured to receive a clock voltage input at clock input 814. As shown, charge pump stage 808-1 receives first input voltage 714 as a clock voltage input at clock input 814-1, while charge pump stages 808-2 through 808-N receive second input voltage 716 as a clock voltage input at clock inputs 814-2 through 814-N. Each charge pump stage 808 may be configured to provide an output voltage at output 812 that is a combination of the input voltage and the clock voltage. For instance, the output voltage level may be the input voltage level plus the clock voltage level. Thus, by selecting a first number of charge pump stages 808 that receive first input voltage 714 (e.g., a temperature-dependent voltage such as a PTAT voltage) as the clock voltage input and a second number of charge pump stages 808 that receive second input voltage 716 (e.g., a temperature-invariant voltage such as a bandgap voltage) as the clock voltage input, charge pump 806 may be configured to output any particular linear combination of first input voltage 714 and second input voltage 716. The output of charge pump 806 may be output by control circuit 802 as a bias voltage for SPAD 804. Thus, the particular linear combination of first input voltage 714 and second input voltage 716 may be selected to vary at a same rate of change as the breakdown voltage to keep a constant overvoltage and sensitivity for SPAD 804.

As an example, the breakdown voltage of SPAD 804 may be determined to vary with temperature as described by an equation such as $V_{bd}=21+0.03*T$, where $V_{bd}$ is the breakdown voltage (in volts (V)) and T is the temperature (in Celsius). This equation describing the breakdown voltage variance may be determined in any suitable manner, such as measuring breakdown voltages at various temperatures and fitting a line to the measurements.

The output of charge pump 806 may be described by $V_{out}=V_{in}$ $M*V_{clk,PTAT}+N*V_{clk,BG}$, where $V_{out}$ is the output voltage, $V_{in}$ is the input voltage of charge pump 806, M is the number of charge pump stages 808 that receive a PTAT voltage as the clock voltage, $V_{clk,PTAT}$ is a voltage level of the PTAT voltage, N is the number of charge pump stages 808 that receive a bandgap voltage as the clock voltage, and $V_{clk,BG}$ is a voltage level of the bandgap voltage. In this example, control circuit 802 may be configured to output a bias voltage that varies at the same rate of change as the breakdown voltage and remains 3 V above the breakdown voltage.

Thus, the bias voltage may be described by an equation $V_{bias}=24+0.03*T$, where $V_{bias}$ is the bias voltage. The number 24 in the equation would allow the bias voltage to be maintained 3 V above the breakdown voltage, assuming that the breakdown voltage is defined to be $V_{bd}=21+0.03*T$ as described above. To output a bias voltage described by this $V_{bias}$ equation, charge pump 806 may include twenty-one charge pump stages 808. Five charge pump stages 808 may receive the PTAT voltage as the clock voltage and 16 charge pump stages 808 may receive the bandgap voltage as the clock voltage. Charge pump stage 808-1 may also receive the PTAT voltage as an input voltage. With a PTAT voltage that is 1.5 V at room temperature and a 1.5 V bandgap voltage, charge pump 806 with such a configuration may provide output voltage 816 that corresponds to the equation for the bias voltage as described. Further, as the temperature changes, the PTAT voltage may vary proportional to the temperature. The configuration of charge pump stages 808 may allow charge pump 806 to provide output voltage 816 that varies at the same rate as the breakdown voltage of SPAD 804. Output voltage 816 may thus be provided to SPAD 804 as the bias voltage.

Figure 9:
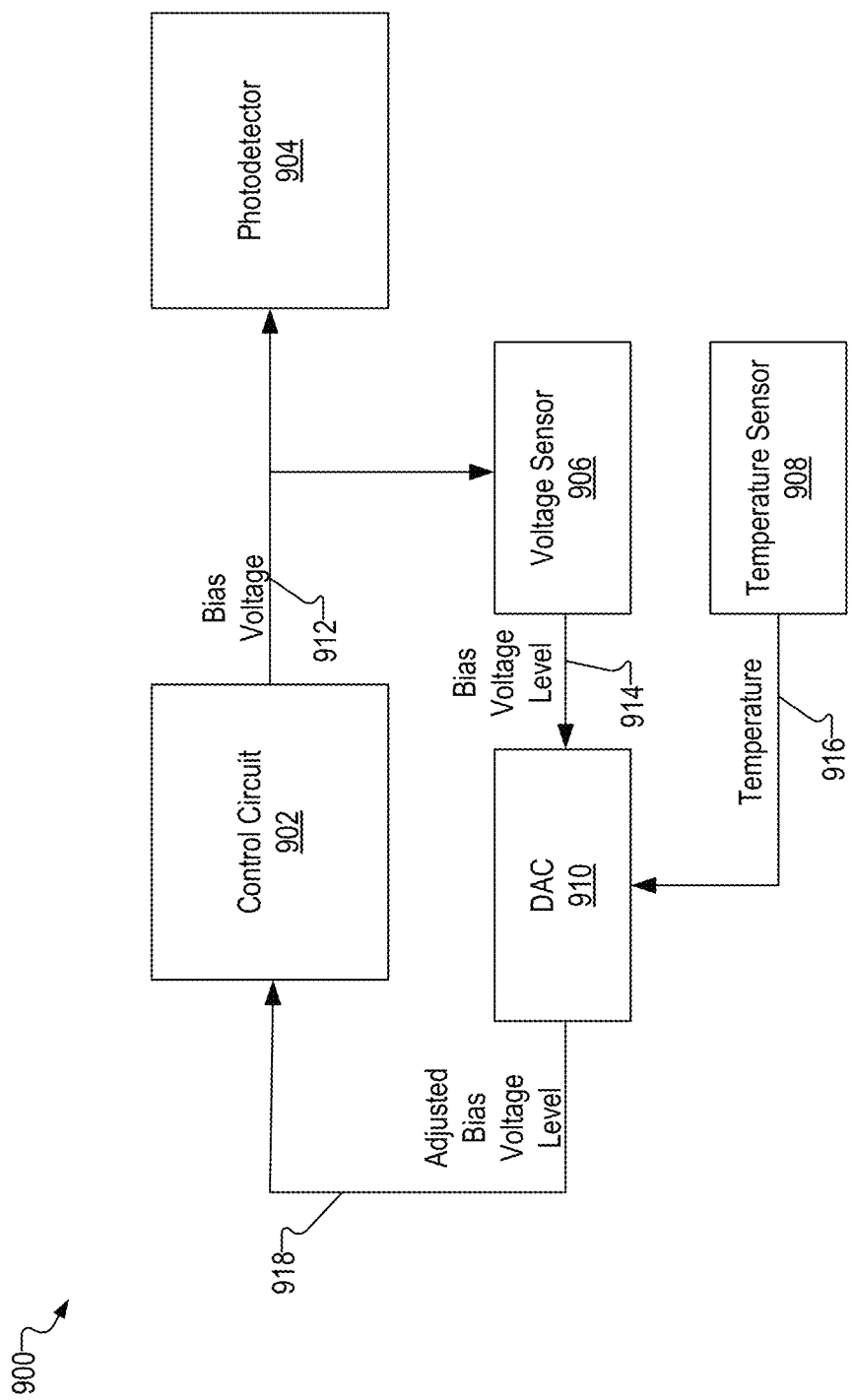

FIG. 9 shows another configuration 900 of components of an optical measurement system (e.g., an implementation or portion of optical measurement system 100). Configuration 900 includes a control circuit 902 (e.g., an implementation or portion of control circuit 204 and/or processor 508) and a photodetector 904 (e.g., an implementation of photodetector 106, SPAD circuit 202, etc.). Configuration 900 also includes a voltage sensor 906, a temperature sensor 908, and a digital-to-analog converter (DAC) 910.

In configuration 900, control circuit 902 may be configured to output a bias voltage 912 to photodetector 904. Control circuit 902 may be further configured to adjust bias voltage 912 based on temperature so that bias voltage 912 remains a predetermined voltage level above a breakdown voltage level of photodetector 904. Configuration 900 may include a feedback loop that includes control circuit 902, voltage sensor 906, temperature sensor 908, and DAC 910.

Voltage sensor 906 may receive bias voltage 912 and measure the voltage level of bias voltage 912. Voltage sensor 906 may output a signal 914 representative of the measured voltage level of bias voltage 912 to DAC 910. Temperature sensor 908 may be configured to measure a temperature associated with the optical measurement system (e.g., within a vicinity of photodetector 904) and output a signal 916 representative of the measured temperature. DAC 910 may receive signal 914 as well as a signal 916.

DAC 910 may determine, based on the measured temperature, an adjusted bias voltage level for control circuit 902 to output as bias voltage 912 that would maintain the predetermined voltage level above the breakdown voltage. DAC 910 may determine adjusted bias voltage level in any suitable manner, such as a lookup table, an equation defining the rate of change of the breakdown voltage, receiving a measurement of the breakdown voltage, etc. DAC 910 may provide a signal 918 representative of the adjusted bias voltage level to control circuit 902. In response, control circuit 902 may adjust the voltage level of bias voltage 912 to provide to photodetector 904.

In some examples, control circuit 902 may receive a first input voltage that is temperature dependent and a second input voltage that is temperature invariant and adjust the voltage level of bias voltage 912 in a closed loop manner. For example, control circuit 902 may adjust a combination of the first input voltage and the second input voltage to output the corresponding voltage level of bias voltage 912 that is the predetermined voltage level greater than the breakdown voltage of photodetector 904.

Figure 10:
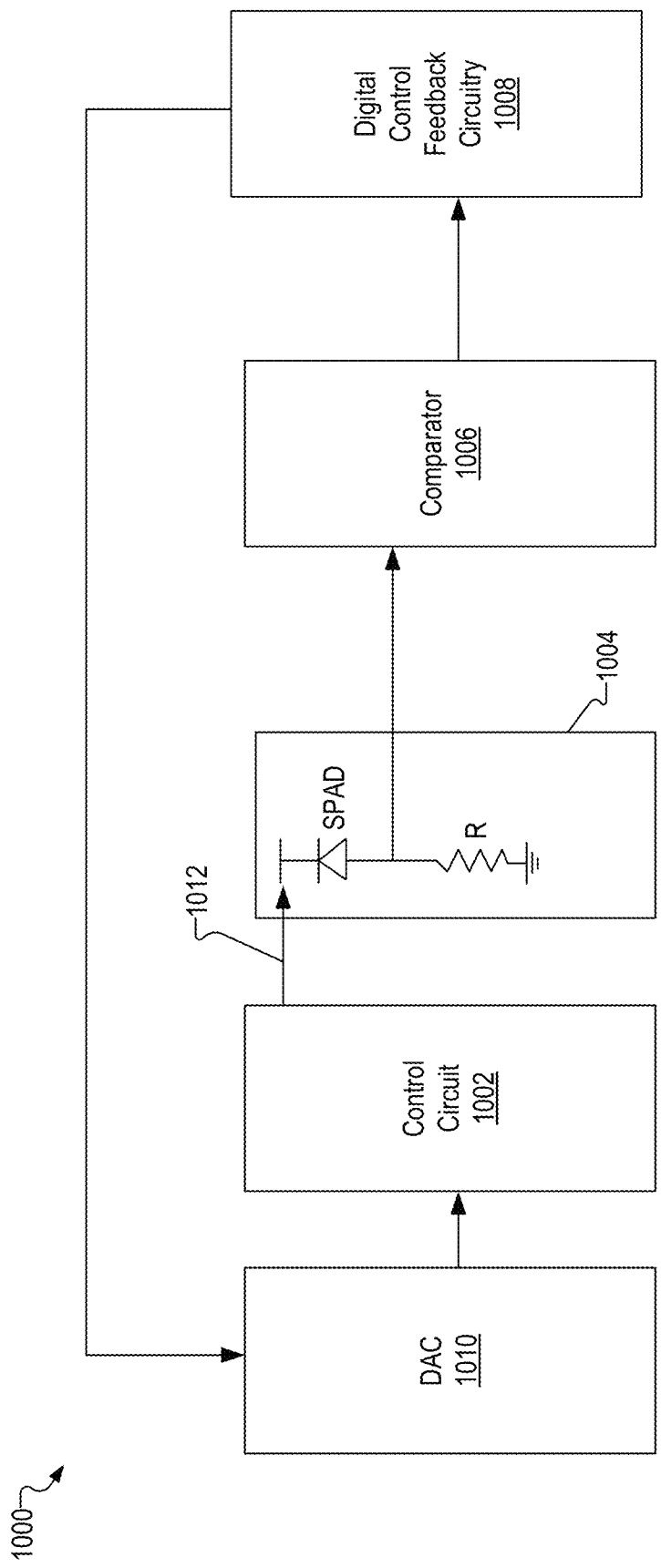

FIG. 10 shows another configuration 1000 of components of an optical measurement system (e.g., an implementation or portion of optical measurement system 100). Configuration 1000 includes a control circuit 1002 (e.g., an implementation or portion of control circuit 204 and/or processor 508) and a SPAD circuit 1004 (e.g., an implementation of photodetector 106, SPAD circuit 202, etc.). Configuration 1000 also includes a comparator 1006, a digital control feedback circuitry 1008, and a digital-to-analog converter (DAC) 1010. Each of these components may be implemented in any suitable manner.

In configuration 1000, control circuit 1002 may be configured to output a bias voltage 1012 to SPAD circuit 1004. Control circuit 1002 may be further configured to adjust bias voltage 1012 to maintain a predetermined voltage level above a breakdown voltage level of SPAD circuit 1004. Control circuit 1002 may be configured to maintain the predetermined voltage level by measuring an overvoltage level (e.g., a difference between a voltage level of bias voltage 1012 and the breakdown voltage level) of SPAD circuit 1004 and adjusting the voltage level of bias voltage 1012 based on the measured overvoltage level.

Thus, if the temperature increases and the breakdown voltage increases accordingly, the measured overvoltage level may decrease, as the difference between the voltage level of bias voltage 1012 and the breakdown voltage may decrease. In response, control circuit 1002 may increase the voltage level of bias voltage 1012 until the measured overvoltage returns to the predetermined voltage level.

Control circuit 1002 may monitor the overvoltage via a feedback loop including comparator 1006, digital control feedback circuitry 1008, and DAC 1010. When the SPAD of SPAD circuit 1004 is triggered, comparator 1006 may receive a voltage level of an anode of the SPAD, which may represent a measured overvoltage level. Comparator 1006 may compare the measured overvoltage level to a reference voltage (e.g., the predetermined voltage level). Comparator 1006 may output a high value if the measured overvoltage level is higher than the reference voltage and a low value if the measured overvoltage level is lower than the reference voltage (or vice versa). Digital control feedback circuitry 1008 may receive the output of comparator 1006 and output a digital value to DAC 1010 to set an output of control circuit 1002 so that the measured overvoltage level matches the reference voltage.

In some examples, the overvoltage level may be measured on a plurality of SPADs, as there may be some variation in breakdown voltage across SPADs on a detector and/or in an optical measurement system. In such examples, the voltage level of bias voltage 1012 and/or the reference voltage may be adjusted such that bias voltage 1012 is within a margin of error (e.g., a least significant bit of DAC 1010) of the reference voltage, based on a majority of the measured overvoltage levels of the plurality of SPADs.

FIGS. 11-16 illustrate embodiments of a wearable device 1100 that includes elements of the optical detection systems described herein. In particular, the wearable devices 1100 shown in FIGS. 11-16 include a plurality of modules 1102, similar to the modules shown in FIG. 6 as described herein. For example, each module 1102 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors. The wearable devices 1100 may each also include a controller (e.g., controller 112) and a processor (e.g., processor 108) and/or be communicatively connected to a controller and processor. In general, wearable device 1100 may be implemented by any suitable headgear and/or clothing article configured to be worn by a user. The headgear and/or clothing article may include batteries, cables, and/or other peripherals for the components of the optical measurement systems described herein.

Figure 11:
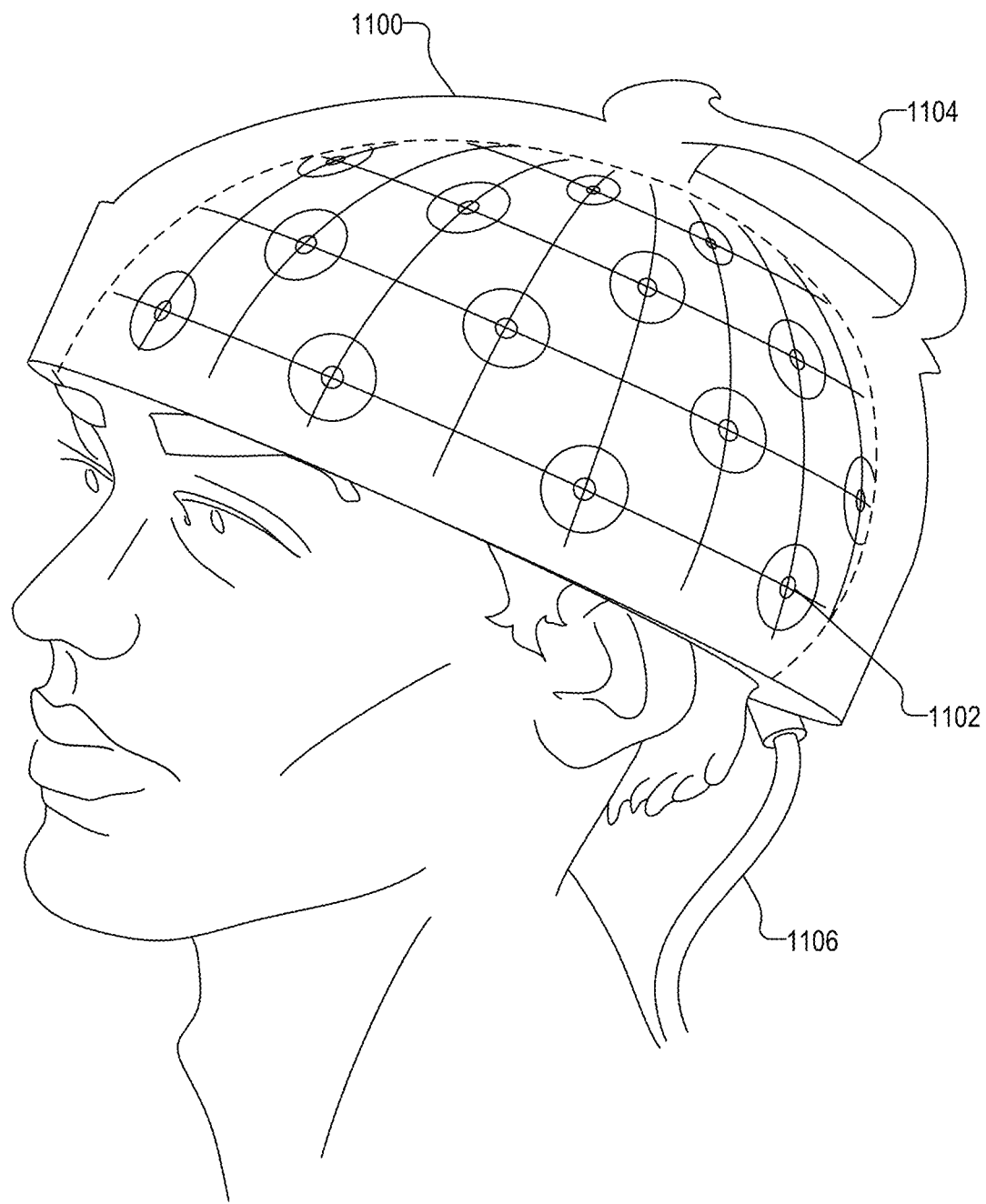
FIGS. 11-16 illustrate embodiments of a wearable device that includes elements of the optical measurement systems described herein.
Figure 12:
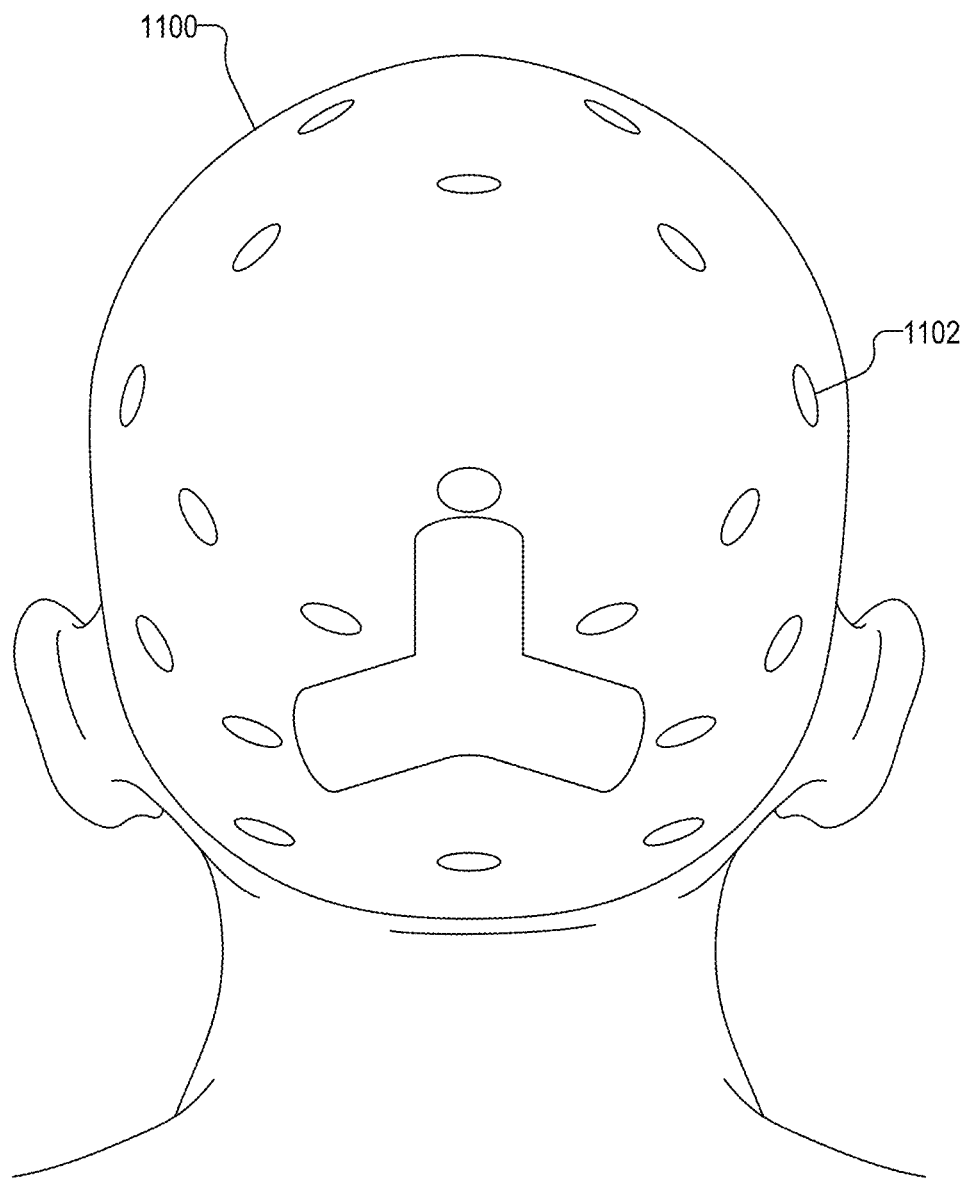
Figure 13:
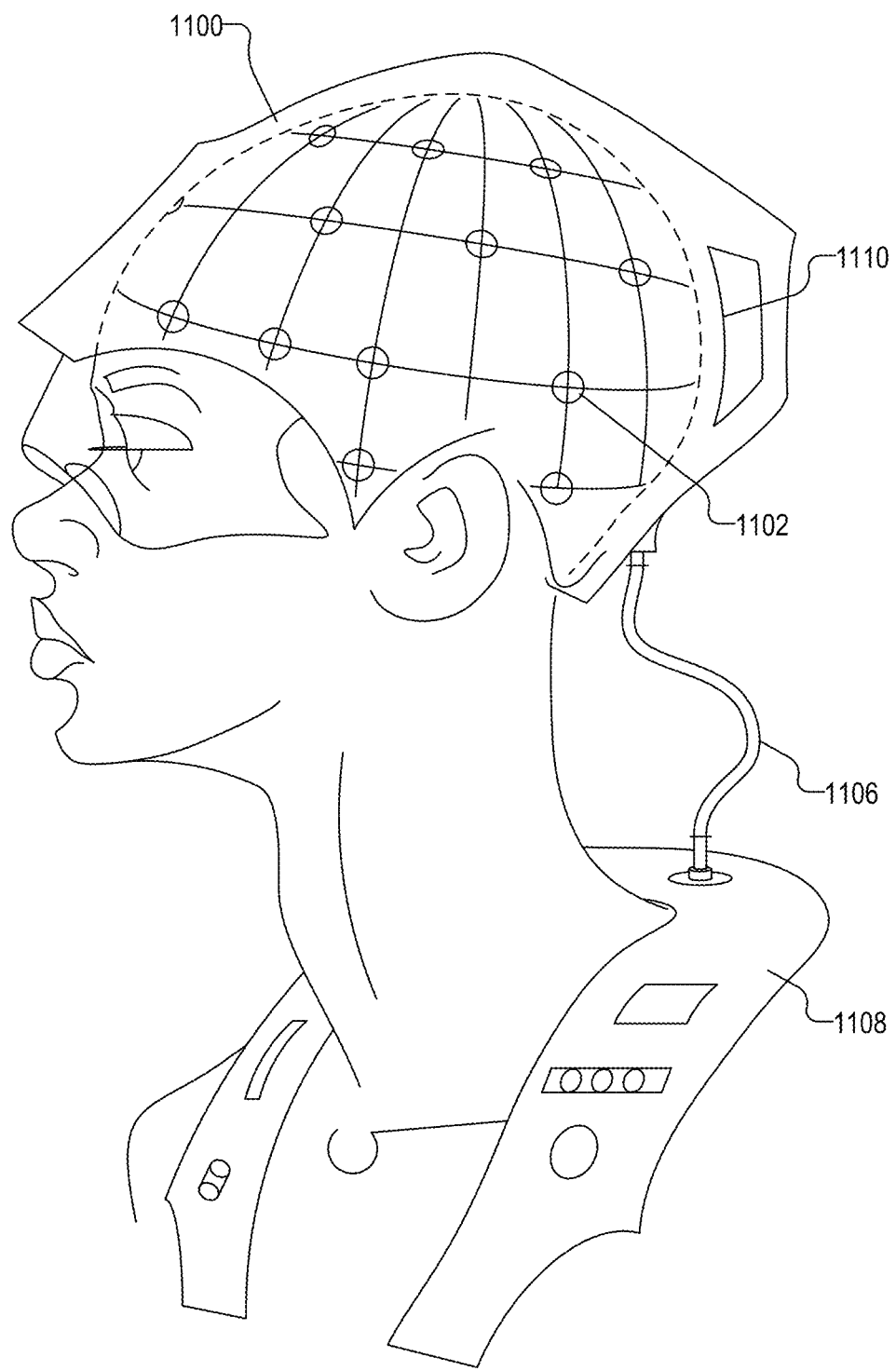

FIG. 11 illustrates an embodiment of a wearable device 1100 in the form of a helmet with a handle 1104. A cable 1106 extends from the wearable device 1100 for attachment to a battery or hub (with components such as a processor or the like). FIG. 12 illustrates another embodiment of a wearable device 1100 in the form of a helmet showing a back view. FIG. 13 illustrates a third embodiment of a wearable device 1100 in the form of a helmet with the cable 1106 leading to a wearable garment 1108 (such as a vest or partial vest) that can include a battery or a hub. Alternatively or additionally, the wearable device 1100 can include a crest 1110 or other protrusion for placement of the hub or battery.

Figure 14:
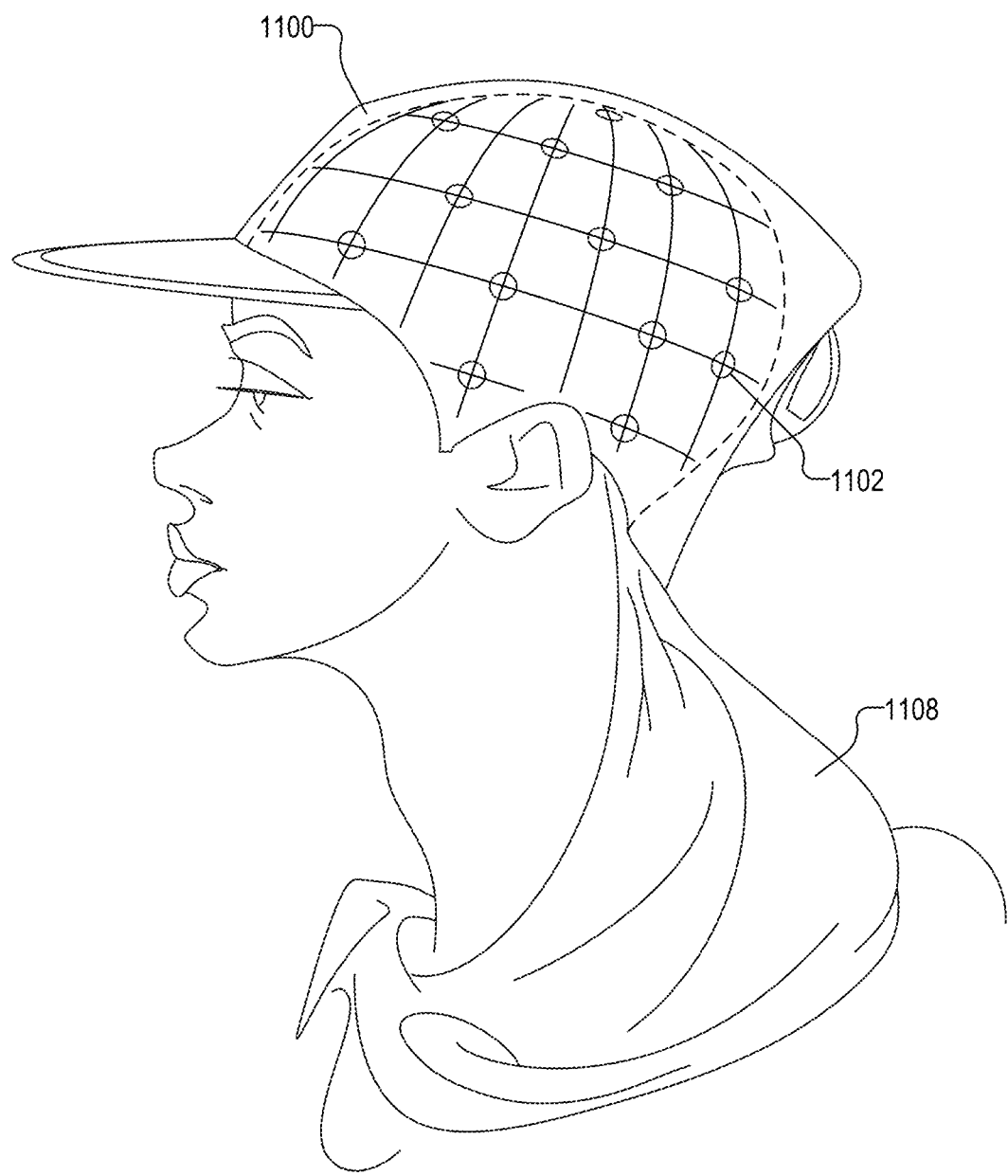
Figure 15:
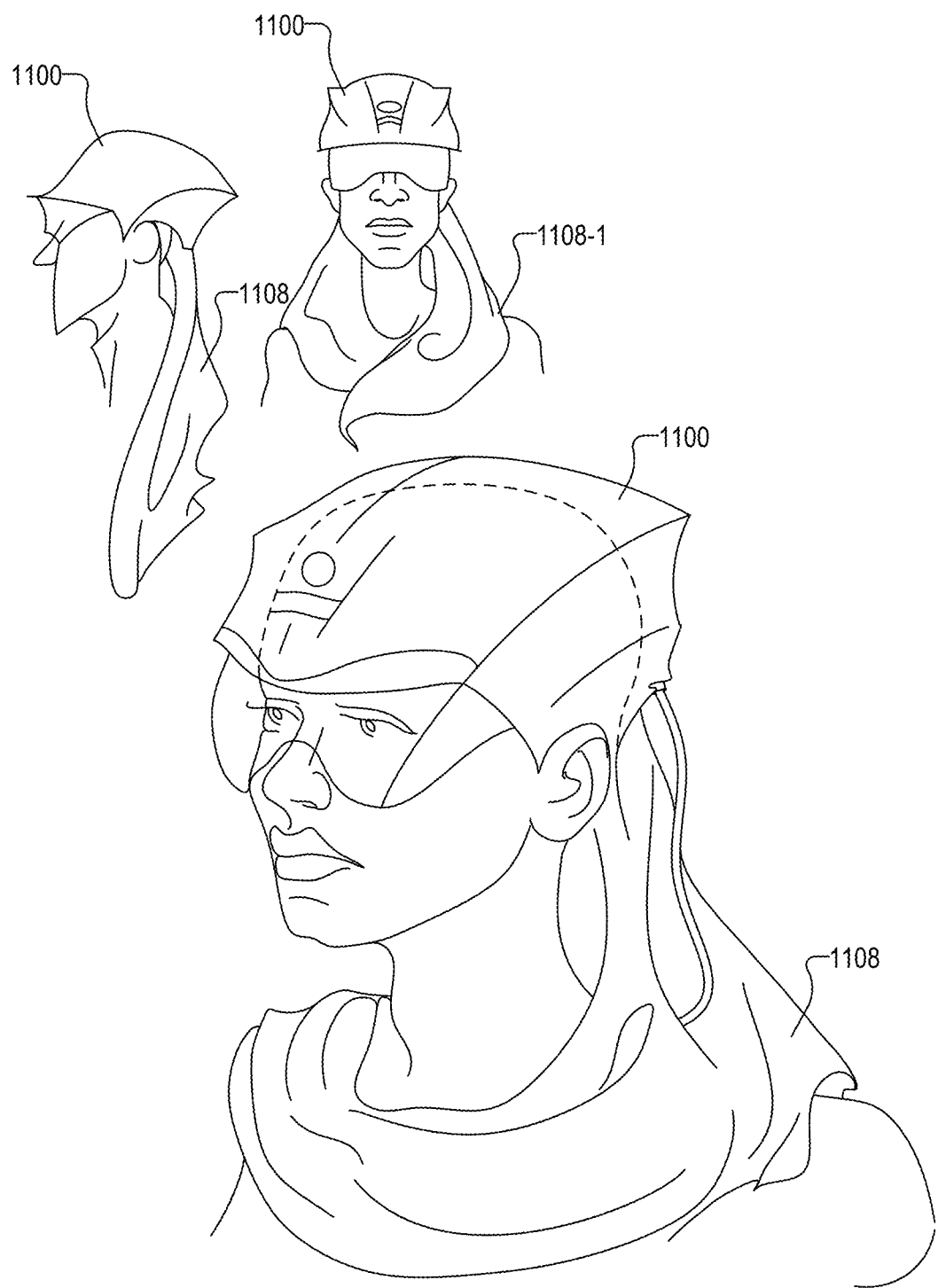
Figure 16:
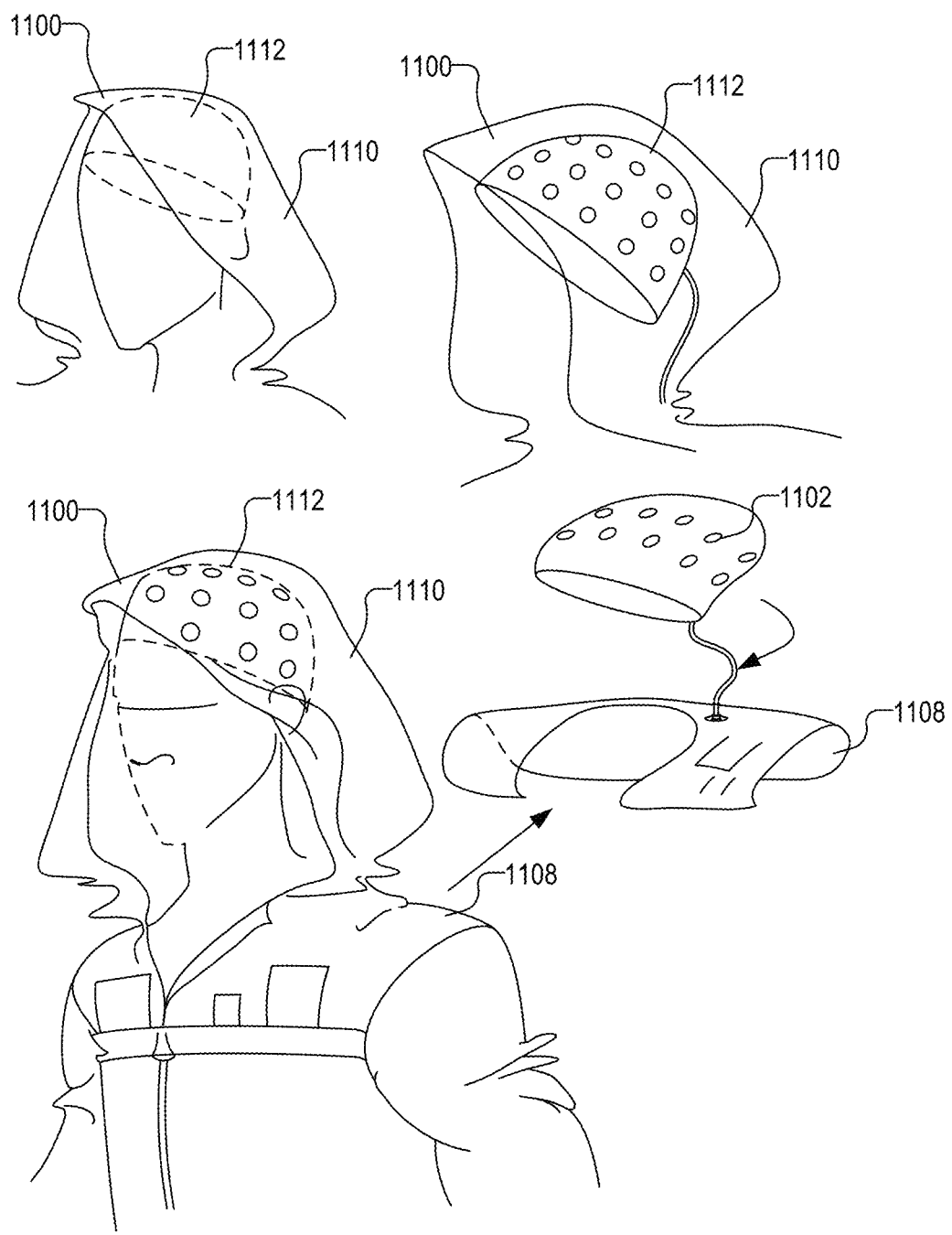

FIG. 14 illustrates another embodiment of a wearable device 1100 in the form of a cap with a wearable garment 1108 in the form of a scarf that may contain or conceal a cable, battery, and/or hub. FIG. 15 illustrates additional embodiments of a wearable device 1100 in the form of a helmet with a one-piece scarf 1108 or two-piece scarf 1108-1. FIG. 16 illustrates an embodiment of a wearable device 1100 that includes a hood 1110 and a beanie 1112 which contains the modules 1102, as well as a wearable garment 1108 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 17:
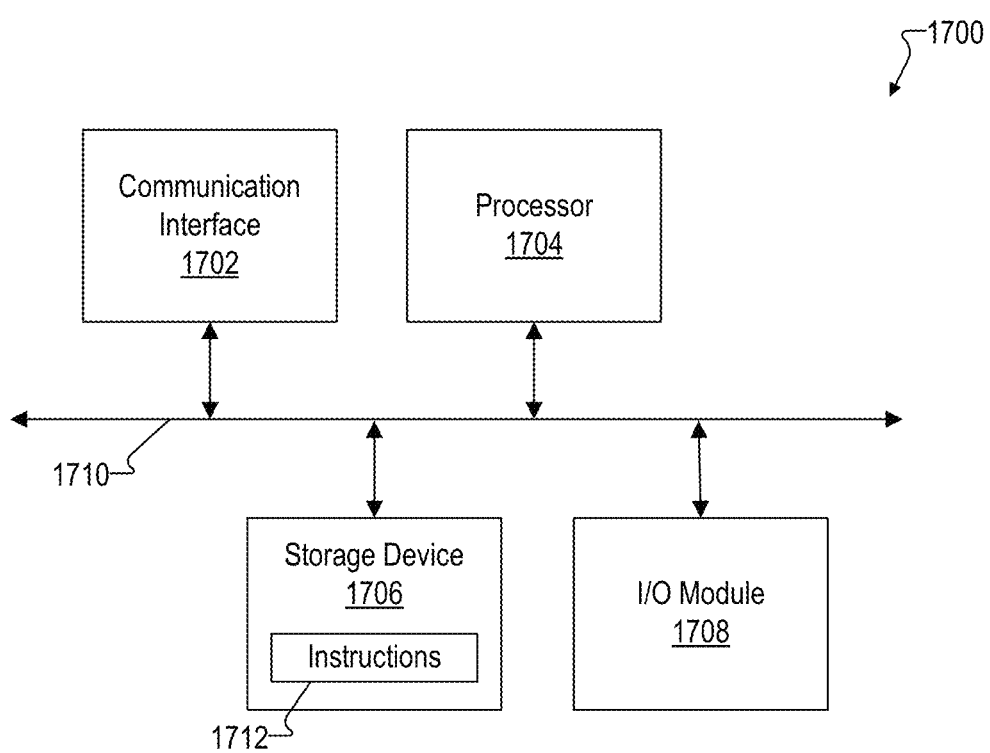
FIG. 17 illustrates an exemplary computing device.

FIG. 17 illustrates an exemplary computing device 1700 that may be specifically configured to perform one or more of the processes described herein. Any of the systems, units, computing devices, and/or other components described herein may be implemented by computing device 1700.

As shown in FIG. 17, computing device 1700 may include a communication interface 1702, a processor 1704, a storage device 1706, and an input/output ("I/O") module 1708 communicatively connected one to another via a communication infrastructure 1710. While an exemplary computing device 1700 is shown in FIG. 17, the components illustrated in FIG. 17 are not intended to be limiting. Additional or alternative components may be used in other embodiments. Components of computing device 1700 shown in FIG. 17 will now be described in additional detail.

Communication interface 1702 may be configured to communicate with one or more computing devices. Examples of communication interface 1702 include, without limitation, a wired network interface (such as a network interface card), a wireless network interface (such as a wireless network interface card), a modem, an audio/video connection, and any other suitable interface.

Processor 1704 generally represents any type or form of processing unit capable of processing data and/or interpreting, executing, and/or directing execution of one or more of the instructions, processes, and/or operations described herein. Processor 1704 may perform operations by executing computer-executable instructions 1712 (e.g., an application, software, code, and/or other executable data instance) stored in storage device 1706.

Storage device 1706 may include one or more data storage media, devices, or configurations and may employ any type, form, and combination of data storage media and/or device. For example, storage device 1706 may include, but is not limited to, any combination of the non-volatile media and/or volatile media described herein. Electronic data, including data described herein, may be temporarily and/or permanently stored in storage device 1706. For example, data representative of computer-executable instructions 1712 configured to direct processor 1704 to perform any of the operations described herein may be stored within storage device 1706. In some examples, data may be arranged in one or more databases residing within storage device 1706.

I/O module 1708 may include one or more I/O modules configured to receive user input and provide user output. I/O module 1708 may include any hardware, firmware, software, or combination thereof supportive of input and output capabilities. For example, I/O module 1708 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1708 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1708 is configured to provide graphical data to a display for presentation to a user. The graphical data may be representative of one or more graphical user interfaces and/or any other graphical content as may serve a particular implementation.

Figure 18:
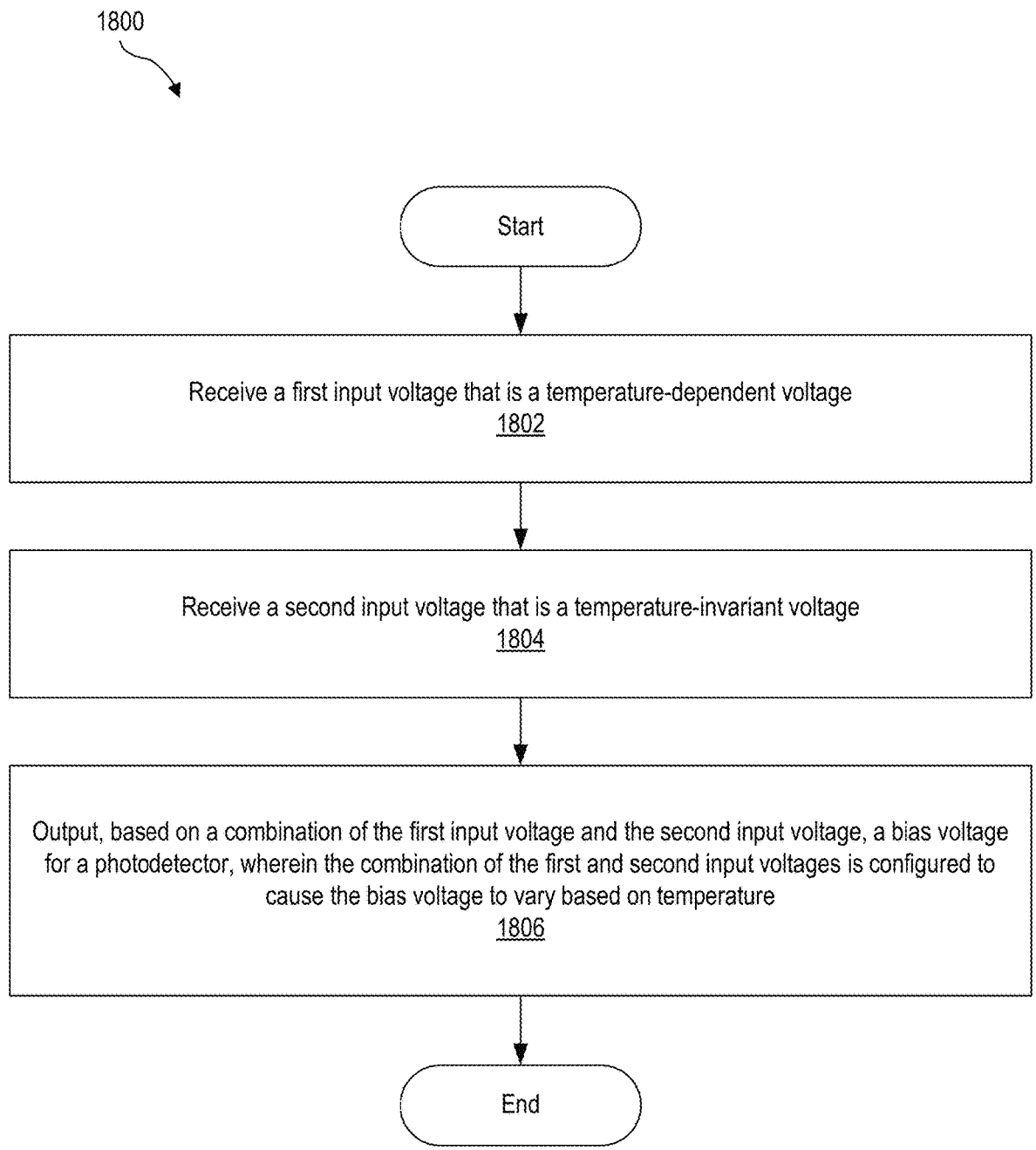
FIG. 18 illustrates an exemplary method.

FIG. 18 illustrates an exemplary method 1800 that may be performed by control circuit 702 and/or any implementation thereof. While FIG. 18 illustrates exemplary operations according to one embodiment, other embodiments may omit, add to, reorder, and/or modify any of the operations shown in FIG. 18. Each of the operations shown in FIG. 18 may be performed, or repeated as needed for each respective module located in its respective slot on the wearable device, in any of the ways described herein.

In operation 1802, a control circuit of an optical measurement system receives a first input voltage that is a temperature-dependent voltage.

In operation 1804, the control circuit receives a second input voltage that is a temperature-invariant voltage.

In operation 1806, the control circuit outputs, based on a combination of the first input voltage and the second input voltage, a bias voltage for a photodetector, wherein the combination of the first and second input voltages is configured to cause the bias voltage to vary based on temperature.

An exemplary optical measurement system described herein includes a light source configured to emit light directed at a target. The optical measurement system further includes a photodetector configured to detect a photon of the light after the light is scattered by the target. The optical measurement system further includes a control circuit configured to receive a first input voltage that is a temperature-dependent voltage. The control circuit is further configured to receive a second input voltage that is a temperature-invariant voltage. The control circuit is further configured to output, based on a combination of the first input voltage and the second input voltage, a bias voltage for the photodetector, wherein the combination of the first and second input voltages is configured to cause the bias voltage to vary based on temperature.

An exemplary system described herein includes a single photon avalanche diode (SPAD) configured to detect a photon from a light pulse after the light pulse reflects off a target within a body. The system further includes a fast gating circuit configured to arm and disarm the SPAD. The system further includes a laser diode and a control circuit. The control circuit is configured to receive a first input voltage that is a temperature-dependent voltage. The control circuit is further configured to receive a second input voltage that is a temperature-invariant voltage. The control circuit is further configured to output, based on a combination of the first input voltage and the second input voltage, a bias voltage for the photodetector, wherein the combination of the first and second input voltages is configured to cause the bias voltage to vary based on temperature.

An exemplary wearable system described herein a head-mountable component configured to be attached to a head of the user. The head-mountable component includes a photodetector configured to detect a photon from a light pulse after the light pulse reflects off a target within the head. The wearable system further includes a laser diode and a control circuit. The control circuit is configured to receive a first input voltage that is a temperature-dependent voltage. The control circuit is further configured to receive a second input voltage that is a temperature-invariant voltage. The control circuit is further configured to output, based on a combination of the first input voltage and the second input voltage, a bias voltage for the photodetector, wherein the combination of the first and second input voltages is configured to cause the bias voltage to vary based on temperature.

An exemplary method described herein includes receiving, by a control circuit, a first input voltage that is a temperature-dependent voltage. The method further includes receiving, by the control circuit, a second input voltage that is a temperature-invariant voltage. The method further includes outputting, by the control circuit and based on a combination of the first input voltage and the second input voltage, a bias voltage for a photodetector, wherein the combination of the first and second input voltages is configured to cause the bias voltage to vary based on temperature.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
   a light source configured to emit light directed at a target;
   a photodetector configured to detect a photon of the light after the light is scattered by the target; and
   a control circuit configured to:
      receive a first input voltage that is a temperature-dependent voltage;
      receive a second input voltage that is a temperature-invariant voltage; and
      output, based on a combination of the first input voltage and the second input voltage, a bias voltage for the photodetector, wherein the combination of the first and second input voltages is configured to cause the bias voltage to vary based on temperature.

2. The optical measurement system of claim 1, wherein the combination of the first and second input voltages is based on a breakdown voltage of the photodetector such that the bias voltage is configured to vary based on the breakdown voltage.

3. The optical measurement system of claim 2, wherein:
   the breakdown voltage is a temperature-dependent voltage; and
   the control circuit is configured to maintain the bias voltage a predetermined voltage level above the breakdown voltage.

4. The optical measurement system of claim 1, wherein the control circuit comprises a charge pump configured to output the bias voltage.

5. The optical measurement system of claim 4, wherein:
   the first input voltage is a proportional-to-absolute temperature (PTAT) voltage;
   the second input voltage is a bandgap voltage; and
   the charge pump comprises a plurality of charge pump stages cascaded together including a first charge pump stage and a second charge pump stage,
      the first charge pump stage configured to receive, as a clock voltage of the first charge pump stage, the PTAT voltage, and
      the second charge pump stage configured to receive, as a clock voltage of the second charge pump stage, the bandgap voltage.

6. The optical measurement system of claim 1 further comprising an array of photodetectors including the photodetector, and
   wherein the control circuit configured to output the bias voltage for the photodetector includes outputting the bias voltage for the array of photodetectors.

7. The optical measurement system of claim 1, wherein the photodetector comprises:
   a single photon avalanche diode (SPAD); and
   a fast gating circuit configured to arm and disarm the SPAD.

8. The optical measurement system of claim 1, wherein the photodetector is included in a wearable device configured to be worn by a user.

9. The optical measurement system of claim 8, wherein the wearable device includes a head-mountable component configured to be worn on a head of a user.

10. A method comprising:
    receiving, by a control circuit, a first input voltage that is a temperature-dependent voltage;
    receiving, by the control circuit, a second input voltage that is a temperature-invariant voltage; and
    outputting, by the control circuit and based on a combination of the first input voltage and the second input voltage, a bias voltage for a photodetector, wherein the combination of the first and second input voltages is configured to cause the bias voltage to vary based on temperature.

11. The method of claim 10, wherein the combination of the first and second input voltages is based on a breakdown voltage of the photodetector such that the bias voltage is configured to vary based on the breakdown voltage.

12. The method of claim 11, wherein:
    the breakdown voltage is a temperature-dependent voltage; and
    the outputting the bias voltage comprises maintaining, by the control circuit, the bias voltage at a predetermined voltage level above the breakdown voltage.

13. The method of claim 10, wherein:
    the control circuit comprises a charge pump; and
    the outputting the bias voltage comprises providing an output of the charge pump.

14. The method of claim 13, wherein:
    the first input voltage is a proportional-to-absolute temperature (PTAT) voltage;
    the second input voltage is a bandgap voltage;
    the charge pump comprises a plurality of charge pump stages cascaded together including a first charge pump stage and a second charge pump stage;
    the receiving the first input voltage by the control circuit comprises the first charge pump stage receiving, as a clock voltage input of the first charge pump stage, the PTAT voltage, and
    the receiving the second input voltage by the control circuit comprises the second charge pump stage receiving, as a clock voltage input of the second charge pump stage, the bandgap voltage.

15. The method of claim 13, wherein the outputting the bias voltage for the photodetector comprises outputting the bias voltage for an array of photodetectors including the photodetector.

* * * * *